US00PP37456P2

(12) United States Plant Patent
Grazzini

(10) Patent No.: US PP37,456 P2
(45) Date of Patent: Jun. 9, 2026

(54) COLEUS PLANT NAMED 'G22031'

(50) Latin Name: *Coleus scutellarioides*
Varietal Denomination: G22031

(71) Applicant: Richard A. Grazzini, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 19/354,481

(22) Filed: Oct. 9, 2025

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

(56) References Cited

U.S. PATENT DOCUMENTS

PP27,077 P3 * 8/2016 Clark ..... A01H 6/50
Plt./321

* cited by examiner

*Primary Examiner* — Karen M Redden

(57) ABSTRACT

A new and distinct cultivar of *Coleus* plant named 'G22031' is disclosed, characterized by a compact, densely branched plant habit forming an ovate-globose shape. Foliage has a bright pink central blotch radiating into a large dark violet blotch surrounded by bright a golden green picotee. Floral initiation begins in late October, or not at all, at 41N latitude, under natural daylength. Foliage is strongly resistant to *Coleus* downy mildew (CDM), caused by *Peronospora choii*. The new cultivar is a *Coleus*, typically produced as an outdoor ornamental plant or for garden or container uses.

1 Drawing Sheet

Latin name of the genus and species: *Coleus scutellarioides*.

Variety denomination: 'G22031'.

BACKGROUND OF THE INVENTION

The new cultivar is the product of a planned breeding program conducted by the inventor. New variety 'G22031' is a seedling selected from seed harvested as an isolated mass population in October 2021 and sown in January 2022. The isolated mass population consisted of internally developed *Coleus* varieties and breeding lines, and was grown in containers in an isolated location at a research nursery in Bellefonte, PA. The new variety was found and selected by the inventor in March of 2022 at the same research greenhouse in Bellefonte, Pennsylvania.

Asexual reproduction of the new cultivar 'G22031' by terminal vegetative cuttings was performed at the same nursery in Bellefonte, Pennsylvania in March of 2022. Subsequent asexual reproduction, both by terminal cuttings and tissue culture has shown that the unique features of this cultivar are stable and reproduced true to type through successive generations.

SUMMARY OF THE INVENTION

The cultivar 'G22031' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22031'.

These characteristics in combination distinguish 'G22031' as a new and distinct *Coleus* cultivar:

1. Compact, uniform, densely branched habit.
2. Plant is typically globular to ovate in shape, 30 to 32 in (76 to 81 cm) in both height and 24 to 28 inches (61 to 71 cm) in width.
3. Foliage with a bright pink central blotch radiating into a large dark violet blotch surrounded by bright golden green picotee.
4. Foliage is strongly resistant to *Coleus* downy mildew (CDM), caused by *Peronospora choii*. No symptoms of CDM have been observed on plants of 'G22031' since its selection in 2022 in greenhouse, outdoor container, or outdoor in-ground trials. In those same trials, CDM-susceptible *Coleus* varieties were observed to suffer foliage losses due to CDM infection at rates from 25% to 100%.
5. Floral initiation begins in late October (or not at all), at 41N latitude, under natural daylengths.

PARENT COMPARISON

Parental varieties cannot be identified.

COMMERCIAL COMPARISON

'G22031' can be compared to the commercially known variety *Coleus* 'Dallas', unpatented. These plants are similar in most horticultural characteristics. However, plants of the new cultivar 'G22031' differ in the following ways:

1. Foliage of 'G22031' is multi-colored; foliage of 'Dallas' is dark violet.

2. Plant shape of 'G22031' is an upright globe, plant shape of 'Dallas' is a squat globe.
3. 'G22031' exhibits strong tolerance to *Coleus* downy mildew (CDM) caused by *Peronospora choi*; this comparator exhibits little if any tolerance for CDM infection.

'G22031' can also be compared to the commercially known variety *Coleus* 'UF09-8-37', U.S. Plant Pat. No. 27,077. These cultivars are similar in most horticultural characteristics. However, plants of the new cultivar 'G22031' differ in the following ways:

1. Foliage of 'G22031' is multi colored; foliage of 'UF09-8-37' is orange-red.
2. Plants of 'G22031' are approximately 25% taller and wider than plants of 'UF09-8-37'.
3. Stems of 'G22031' are more flexible than stems of this comparator, resulting in less damage during shipping.

BRIEF DESCRIPTION OF THE PHOTOGRAPH

The accompanying photograph illustrates a close-up view of the mature foliage on a plant of about 5 months old grown in Columbus, OH. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G22031' plants grown outdoors during Summer in Camarillo, California. The growing temperature ranged from about 7° C. to 28° C. during the day and from about 5° C. to 18° C. during the night. General light conditions are bright, normal sunlight. Measurements and numerical values represent averages of typical plant types. Plants are approximately 4 months old from a rooted cutting. No chemical or photoperiodic treatments were given.

Botanical classification: *Coleus scutellarioides* 'G22031'.

PROPAGATION

Root description: Fine, well-branched, fibrous, becoming slightly woody with age. Colored near Greyed-Yellow-161D and White 155A.

PLANT

Growth habit: Tender herbaceous perennial. Ovate-globular. Dense branching and foliage.
Height: Approximately 38 cm.
Plant spread: Approximately 32 cm.
Growth rate: Moderate.
Branching characteristics: Basal and lateral branching. Very well branched both basally and laterally.
Length of branches: Approximately 9 to 23 cm.
Diameter branches: Approximately 4 to 5 mm.
Quantity of branches: Approximately 4 to 6 basal branches, each basal branch with 6 to 8 lateral branches.
Texture of lateral branches: Puberulent.
Color of lateral branches: Near RHS Yellow-Green 144C. Nodes flushed Greyed-Purple 187C. Some streaks and speckles N187C, generally close to nodes.
Aspect: Approximately 20° to 45° angle from center of plant.
Strength of lateral branches: Moderate.
Internode length: Average range 1.2 to 3.4 cm
Age of plant described: Approximately 4 months old.

FOLIAGE

Arrangement: Opposite.
Average length: Average range 6 to 7 cm.
Average width: 3 cm.
Shape of blade: Ovate.
Apex: Acute.
Base: Attenuate.
Attachment: Attenuate
Margin: Deeply crenate. Crenations about 7 mm deep.
Texture of top surface: Near velvety.
Texture of bottom surface: Glabrous with slightly protruding veins.
Foliage color:
*Young foliage upper side*.—Innermost central irregular elongated blotch or heavy streaks Red-Purple 61B and 61C surrounded by a large irregular elongated blotch or heavy streaks of Greyed-Purple 187A flushed N187A. Basal blotch 10D. Along mid vein Yellow 10D bleeding into center during late Summer. Thick marginal picotee Green 143B.
*Young foliage under side*.—Overall Green 143B. Basal blotch 10D, extending up mid vein. Center irregular elongated blotch Red- Purple 58D.
*Mature foliage upper side*.—Innermost central irregular elongated blotch or heavy streaks Red-Purple 61B and 61C surrounded by a large irregular elongated blotch or heavy streaks of Greyed-Purple 187A flushed N187A. Along mid vein Yellow 10D bleeding into center during late Summer. Thick marginal picotee Yellow-Green 144C.
*Mature foliage under side*.—Overall Green 137D Basal blotch Orange 27D. extending up mid vein. Irregular flushing along mid-vein 61C.
Venation:
*Type*.—Pinnate. Young Foliage: Venation color upper side: Base yellow 11D. Center Red-Purple 59C. Uppermost 144B. Venation color under side: Yellow 10D. outmost lateral veins Yellow-Green 144D. Mature Foliage: Venation color upper side: Red-Purple 60A Uppermost 10% Green 137B. Venation color under side: Base Red-Purple 59D. Center Orange 27C. uppermost 20% Green 137D.
Petiole:
*Length*.—Average 2 to 4 cm.
*Diameter*.—Average 4 mm.
*Color*.—Upper: Yellow 10C flushed Red-Purple 59D. Lower surface: Yellow-Green 144D turning Yellow 11D toward leaf blade.
*Texture*.—Glabrous.

INFLORESCENCE

Natural flowering season: Floral initiation may begin in mid to late September at 41N latitude. Flowering may not be observed every year.
Inflorescence type and habit: Terminal raceme.
Individual flowers: Zygomorphic flowers facing outward.
Longevity of individual flowers: About 3 weeks.
Fragrance: None.

Inflorescence size:
*Length.*—7 to 12 cm.
*Width.*—4 cm.
Quantity of flowers per inflorescence: About 12 to 36.
Corolla:
*Shape.*—Bilabiate, tubular.
*Aspect.*—Outward
*Persistence.*—Self-cleaning.
*Size.*—About 15 mm long and 5 mm wide.
Petals:
*Upper lip.*—Width: 7 mm. Length: 5 mm. Apex: Obtuse, rounded, composed of 2 fused lobes. Base: Fused to central petal. Margin: Entire. Texture: Front: Glabrous. Back: Glabrous. Color: Upper surface: RHS Violet-Blue 91D. Lower surface: RHS Violet-Blue 91D.
*Lower lip.*—Width: 5 mm (folded). Length: 1 cm. Apex: Obtuse, rounded. Base: Fused. Margin: Entire. Texture: Front: Glabrous. Back: Glabrous. Color: Upper surface: RHS Violet-Blue N89C. Base 91D. Lower surface: RHS Violet-Blue 90D. Base White N155A.
*Tube.*—Diameter: 3 mm. Length: 5 mm. Color: Inner: RHS Violet-Blue 91D. Outer: RHS Violet-Blue 91D. Texture: Glabrous.
Bud:
*Shape.*—Ovate.
*Color.*—Base Violet-Blue 91D, apex 90A.
*Size.*—5 mm in height and 4 mm in diameter.
*Texture.*—Glabrous.
Calyx: Bell-shaped, composed of 5 sepals fused at base.
Sepals:
*Shape.*—Elliptic.
*Apex.*—Acute.
*Base.*—Fused.
*Margin.*—Entire.
*Length.*—5 mm.
*Width.*—3 mm.
*Texture.*—Glabrous, upper and lower surfaces.
*Color.*—Upper surface: RHS Yellow-Green 145A. Lower surface: RHS Yellow-Green 145B.
Peduncle:
*Shape.*—Quadrate with prominent longitudinal veins.
*Length.*—2 to 5 cm.
*Diameter.*—4 mm.
*Strength.*—Medium.
*Texture.*—Glabrous.
*Color.*—RHS Yellow-Green N144D.
Pedicel:
*Orientation.*—45° to 90° from peduncle.
*Texture.*—Glabrous.
*Length.*—5 to 7 mm.
*Diameter.*—2 mm.
*Color.*—RHS Yellow-Green 144B.
*Strength.*—Medium.

REPRODUCTIVE ORGANS

Androecium:
*Number of stamens.*—4 per flower, non-protruding.
*Filament.*—Unfused segment about 4 mm, colored near White N155C.
*Pollen.*—Not observed.
Gynoecium:
*Pistil number.*—1 per flower.
*Pistil length.*—15 mm.
*Style length.*—8 mm.
*Style color.*—RHS White N155C.
*Stigma shape.*—Two-parted
*Stigma color.*—White N155C.
*Ovary color.*—RHS Yellow-Green N144D.

OTHER CHARACTERISTICS

Disease resistance: Foliage is strongly resistant to *Coleus* downy mildew (CDM), caused by *Peronospora choii*. No symptoms of CDM have been observed on new variety 'G21015' since its selection in 2021 in greenhouse, outdoor container, or outdoor in-ground trials. In those same trials, CDM-susceptible *Coleus* varieties were observed to suffer foliage losses due to CDM infection at rates from 25% to 100%. Neither resistance nor susceptibility to other diseases or to pests normal to *Coleus* have been observed in this cultivar.
Drought tolerance and temperature tolerance: No tolerance for drought. Tender perennial, USDA zones 10-11. Summer annual in colder zones.
Fruit/seed production: Not observed to date.

What is claimed is:

1. A new and distinct cultivar of *Coleus* plant named 'G22031' as herein illustrated and described.

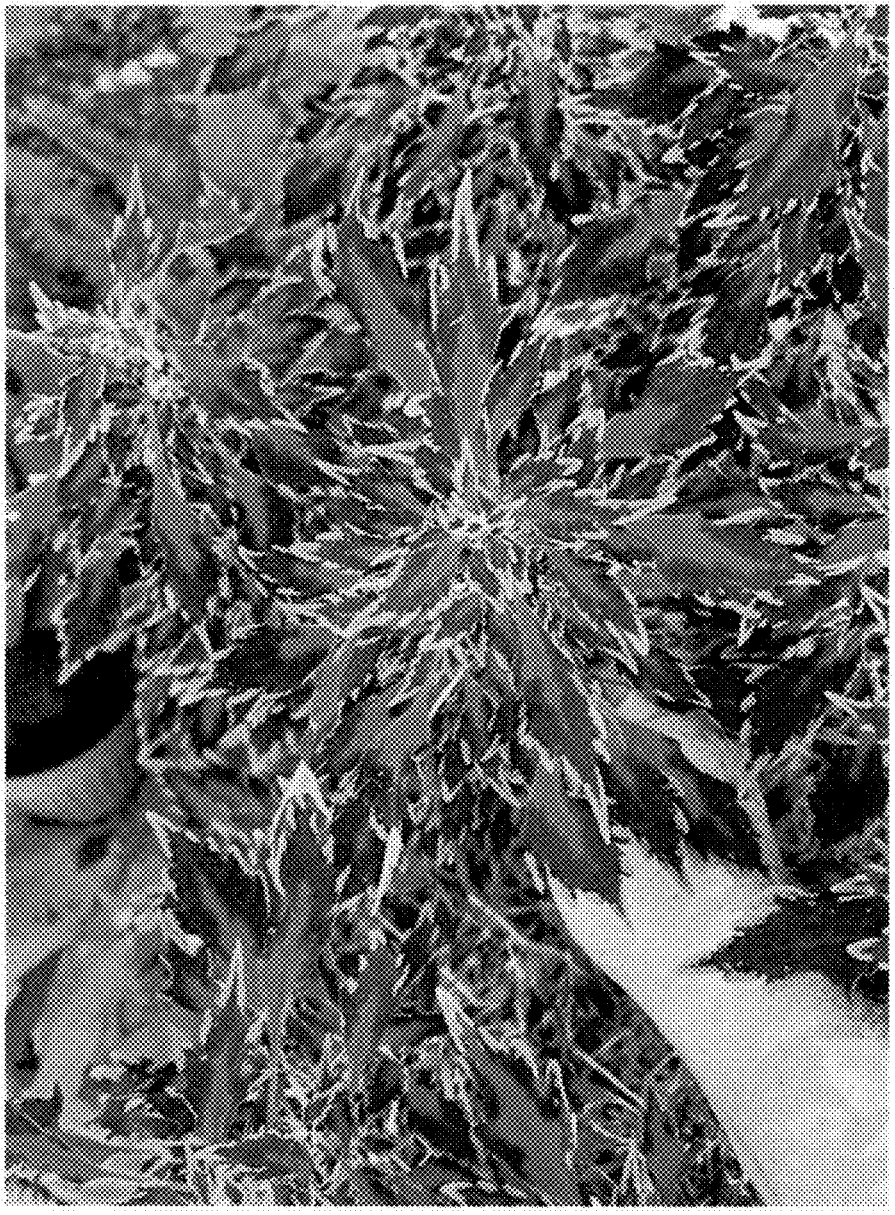

* * * * *